United States Patent [19]

Kahn

[11] 3,940,446

[45] Feb. 24, 1976

[54] DEHYDROGENATION OF ALCOHOLS

[75] Inventor: Samuel Kahn, Rutherford, N.J.

[73] Assignee: Universal Oil Products Company, Des Plaines, Ill.

[22] Filed: July 8, 1971

[21] Appl. No.: 160,902

[52] U.S. Cl. ....... 260/603 HF; 260/598; 260/600 R; 260/602; 260/599; 260/586 R; 260/590 FA; 260/593 R; 260/596; 252/522
[51] Int. Cl.$^2$......................................... C07C 45/16
[58] Field of Search...................... 260/603 HF, 596

[56] References Cited
UNITED STATES PATENTS

| | | | |
|---|---|---|---|
| 2,011,317 | 8/1935 | Groll | 260/603 R |
| 2,083,877 | 6/1937 | Steck et al. | 260/603 R |
| 2,347,636 | 4/1944 | Spence et al. | 260/603 HF |
| 2,400,959 | 5/1946 | Stewart | 260/603 R |
| 2,444,924 | 7/1948 | Farkas et al. | 260/603 HF |
| 3,028,431 | 4/1962 | Webb | 260/603 R |
| 3,216,947 | 11/1965 | Wilkes | 252/192 |

FOREIGN PATENTS OR APPLICATIONS

| | | | |
|---|---|---|---|
| 664,011 | 11/1965 | Belgium | 260/603 R |
| 1,148,219 | 4/1969 | France | 260/603 HF |

OTHER PUBLICATIONS

Clark, Modern Organic Chemistry, 1964, pp. 133–134.

Sabetay et al., Bull. Soc. Chim., Vol. 43, pp. 839–854, 1928.

Kogami et al., Chem. Abstracts, Vol. 72, 100904c, 1970.

Kumano; T., Chem. Abstracts, Vol. 72, 111650t, 1970.

Kolelnikov et al., Chem. Abst., Vol. 70, 5629s, 1969.

Palfray et al., Compt. rend., Vol. 212, pp. 911–913, 1941.

Grimberg; M., Chemical Abstracts, Vol. 64, Col. 6397, 1966.

Primary Examiner—James O. Thomas, Jr.
Assistant Examiner—R. H. Liles
Attorney, Agent, or Firm—James R. Hoatson, Jr.; Bernard L. Kramer

[57] ABSTRACT

Dehydrogenating a primary or secondary alcohol to the corresponding aldehyde or ketone in a compound also containing a tertiary alcohol, with survival of said tertiary alcohol, by effecting the dehydrogenation at a temperature of about 200° to about 350°C. in a stirred suspension of dehydrogenation catalyst and high boiling inert liquid.

6 Claims, No Drawings

DEHYDROGENATION OF ALCOHOLS

BACKGROUND OF THE INVENTION

In copending application Ser. No. 883,323, filed Dec. 8, 1969, a process for the dehydrogenation of a primary or secondary alcohol to the corresponding aldehyde or ketone is disclosed. The dehydrogenation is effected in a stirred suspension of catalyst and high boiling inert liquid. In the disclosed process, the reaction is effected at any suitable pressure which conveniently is atmospheric but, when desired, may be super-atmospheric up to 200 psig or more.

DESCRIPTION OF THE INVENTION

While the process disclosed in application Ser. No. 883,323 is very satisfactory for the dehydrogenation of primary or secondary alcohols, the process is not generally satisfactory for the dehydrogenation of such alcohols which also contain a tertiary alcohol grouping. When a tertiary alcohol grouping adjacent to a carbon containing hydrogen is present, it will dehydrate at the relatively high temperatures required for the dehydrogenation of the primary or secondary hydroxyl group. It now has been found that the tertiary alcohol group in such compounds may be preserved by utilizing the same system and preferably by conducting the reaction under vacuum. This discovery is rather surprising because prior art attempts to effect this conversion met with little success.

In a preferred embodiment the present invention relates to a process for the dehydrogenation of a primary or secondary alcohol to the corresponding aldehyde or ketone in a compound also containing a tertiary alcohol, without loss of said tertiary alcohol, which comprises effecting said dehydrogenation at a temperature of from about 200°C. to about 350C. under a vacuum of from about 40 to about 250 mm Hg in contact with a stirred suspension of an alcohol dehydrogenation catalyst in an inert liquid having a boiling point above the dehydrogenation temperature.

As hereinbefore set forth the process of the present invention is utilized for the dehydrogenation of a primary or secondary alcohol in a compound also containing a tertiary alcohol. A preferred compound is hydroxycitronellol which is dehydrogenated to hydroxycitronellal. Hydroxycitronellal is particularly desirable for use as an aroma chemical. However, during dehydrogenation in accordance with prior art methods, dehydration of hydroxycitronellol occurs as a result of increasing the temperature to about 200°C. which is required for the dehydrogenation reaction. The resulting citronellol is dehydrogenated to citronellal and also is accompanied by the undesired side reaction of cyclization to form isopulegol. In any event, the desired hydroxycitronellal is not obtained in satisfactory yields.

Illustrative examples of other alcohols containing both a primary or secondary alcohol and a tertiary alcohol include 2-hydroxy-2-cyclohexylethanol, 3-hydroxy-3-cyclohexylpropanol, 2-hydroxy-2-cyclohexyl-1-methylethanol, 4-hydroxy-4-cyclohexylbutanol, 3-hydroxy-3-cyclohexyl-2-methylpropanol, etc., 2-hydroxy-2-phenylethanol, 3-hydroxy-3-phenylpropanol, 2-hydroxy-2-phenyl-1-methylethanol, 4-hydroxy-4-phenylbutanol, 3-hydroxy-3-phenyl-2-methylpropanol, etc., 3,3-diphenyl-3-hydroxypropanol, 4,4-diphenyl-4-hydroxybutanol, 3,3-diphenyl-3-hydroxy-2-methylpropanol, etc., 2-hydroxy-2-methylpropanol, 3-hydroxy-3-methylbutanol, 2-hydroxy-1,2-dimethylpropanol, 4-hydroxy-4-methylpentanol, 3-hydroxy-1,3-dimethylbutanol, 6-hydroxy-3,5,6-trimethylheptanol, 6-hydroxy-1,3,5,6-tetramethylheptanol, 7-hydroxy-3,6,7-trimethyloctanol, etc.

A generic formula of compounds containing a primary or secondary hydroxyl and a tertiary hydroxyl may be as follows

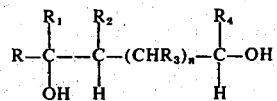

where R and $R_1$ are independently selected from the group consisting of alkyl, aryl, aralkyl and cycloalkyl, $R_2$, $R_3$ and $R_4$ are independently selected from the group consisting of hydrogen, alkyl, aryl, aralkyl and cycloalkyl, and n is integer of 0 to 20 and preferably from 0 to 10. When the group is alkyl, it contains from 1 to 20 and preferably from 1 to 10 carbon atoms. When the group is aryl, it preferably is phenyl, although it may be monoalkylphenyl or dialkylphenyl in which the alkyl contains from 1 to 10 and preferably 1 to 5 carbon atoms each, or the corresponding naphthyl group. When the group is aralkyl, it preferably comprises phenylalkyl in which the alkyl contains from 1 to 10 and preferably 1 to 5 carbon atoms or it may comprise the corresponding naphthyl group. When the group is cycloalkyl, it may contain from 3 to 12 and preferably 5 to 8 carbon atoms in the ring.

The dehydrogenation is effected in a stirred suspension of an alcohol dehydrogenation catalyst in a high boiling liquid. Any suitable alcohol dehydrogenation catalyst is used. A particularly preferred catalyst is cupric oxide and especially when freshly prepared. In one method the cupric oxide catalyst is prepared by precipitating an aqueous solution of a cupric salt, such as the acetate or sulfate, with alkali, filtering and washing free of alkali, then washing with acetone to displace water and finally drying to a constant weight at high vacuum and at a temperature of about 100°C. In some cases advantages appear to also include additional components in the catalyst as, for example, oxides or carbonates of alkali or alkaline earth metals as, for example, sodium carbonate, potassium carbonate, barium carbonate, calcium carbonate, etc. Other catalysts comprise composites of copper or copper oxide with chromium oxide, including copper chromite, and these also containing an additional oxide of zinc, barium, etc., or mixtures thereof.

In accordance with the present invention, dehydrogenation of the alcohol is effected in the presence of a high boiling liquid. The high boiling liquid must be relatively inert under the dehydrogenation conditions and also must have a boiling point above the dehydrogenation temperature so that the material remains liquid and serves the dual purpose of being a suspending medium and a heat transfer agent. A particularly preferred high boiling liquid is mineral oil having an atmospheric or normal boiling point of above about 200°C. and preferably above about 350°C. The end boiling point of the mineral oil generally will be within the range of from about 450° to about 550°C. A number of these mineral oils are available commercially and includes, for example, "Primol 325" which is a colorless mineral having an initial boiling point of 367°C. and an end boiling point of 500°C at 760 mm.

The ratio of high boiling liquid to catalyst is not critical but should be sufficient to provide a readily stirrable mixture. The ratio of high boiling liquid to catalyst thus may range from 2 and preferably from 10 to 100 or up to 1000 or more parts by weight of high boiling liquid per 1 part by weight of catalyst. The catalyst is used in catalytic quantities and, as another feature of the present invention, the catalyst is used in low concentrations. The concentration of catalyst may be within the range of from 0.001 to 0.1 or more parts by weight of catalyst per 1 part by weight of alcohol charged. However, both the high boiling liquid and the catalyst preferably are used in the lowest concentrations suitable for the purpose.

The dehydrogenation is effected at a sufficient temperature to obtain practical conversion. In general, the temperature will be from about 200° to about 350°C. and preferably from about 220° to about 300°C. As hereinbefore set forth, the dehydrogenation is generally effected under vacuum. The specific reduced pressure will be selected to provide a sufficient spread between the boiling point of the reactant-reaction products and the high boiling liquid in order that the unconverted reactant and reaction products may be distilled from the system while retaining the high boiling liquid therein. In general, the dehydrogenation will be effected under a vacuum of from about 40 to about 240 mm Hg and preferably from about 90 to about 150 Hg. With the proper selection of the temperature and the vacuum, a spread of at least 100° C. is readily obtained between the boiling point of the unconverted reactant and reaction products and the boiling point of the high boiling liquid.

The dehydrogenation is effected in any suitable manner and may be in a batch, continuous or semi-continuous system. In one method, a suitable reaction zone is charged with the high boiling liquid and catalyst, then placed under the desired vacuum and heated to the desired temperature. The alcohol feed then is charged to the reactor. The reaction products are removed through a suitable vapor line, then cooled and condensed and finally recovered in a receiving zone. Hydrogen produced in the reaction is removed as an overhead from the receiving zone and may be vented or utilized for any suitable purpose. The condensate in the receiving zone is withdrawn and utilized as such but preferably is fractionated or otherwise processed to recover a fraction predominating in the aldehyde or ketone product.

When desired, a gas purge may be used to aid in stripping unreacted charge and reaction products from the high boiling liquid. The gas purge will be introduced at the bottom of the reaction zone and will strip out the lighter materials. Any suitable inert gas may be used and may be selected from nitrogen, hydrogen, helium, carbon dioxide, etc.

In still another embodiment, when desired, a nonionic surfactant may be introduced into the reaction zone. As will be shown by the following example, lauryl ether of polyoxyethylene was added to the feed. This appeared to raise the catalytic activity of the system. Any other suitable surfactant may be used in this embodiment.

As hereinbefore set forth, in a preferred embodiment the process of the present invention is used for the dehydrogenation of hydroxycitronellol to prepare hydroxycitronellal. Hydroxycitronellal is desired particularly for use in perfumes. Other aldehydes or ketones containing a tertiary alcohol group may be used in perfumery or as intermediates in the preparation of various specialty chemical products.

The following examples are introduced to illustrate further the novelty and utility of the present invention but not with the intention of unduly limiting the same.

EXAMPLE I

This example describes the dehydrogenation of hydroxycitronellol to hydroxycitronellal. The dehydrogenation was effected by using a suspension of cupric oxide catalyst in "Primol 325". As hereinbefore set forth, this mineral oil has a boiling range of 367° to 500°C. at 760 mm. The catalyst was prepared by adding a solution of aqueous cupric acetate to 12.5% aqueous sodium hydroxide. The resultant mixture was stirred and refluxed for about 40 minutes, after which the mixture was cooled, filtered, washed with distilled water, then washed with acetone and finally dried at high vacuum at about 100°C. to a constant weight.

The reaction zone consisted of a 2 liter flask equipped with a mixer, a glass column one-half filled with raschig rings to cut down entrainment, a thermometer and an inlet tube leading to the bottom of the reaction zone. The column was connected to a condenser, receiver, a secondary condensor, then to a dry ice trap and finally to a stream-jet vacuum line via a tee to regulate vacuum.

The reaction zone was charged with 20 g of cupric oxide catalyst and 900 g of "Primol 325". The system then was placed under the desired vacuum and heated to the desired temperature. The hydroxycitronellol feed then was charged at a rate of 200 g/hr. Simultaneously, nitrogen was introduced through the same feed line and the temperature, feed and vacuum were adjusted as required.

In a series of 16 runs of about one hour each, a total of 4748 g of charge, comprising 97.3% by weight of hydroxycitronellol, was processed. The temperature was maintained at about 280°C. and the vacuum at about 116 mm Hg. A total of 4709.8 g of crude reaction product was recovered, which analyzed by G.L.C. to comprise 2865.5 g of hydroxycitronellal. The conversion, based on the G.L.C. values, amounted to 57.5% and the yield amounted to 91.6%. The G.L.C. analysis may be considered as being slightly high. Recalculation based on Dauphin (hydroxylamine) analysis gives a conversion of 55.6% and a yield of 88.5%. In either case, it will be noted that high yield and high conversion are obtained by the novel method of the present invention.

At the end of run 11 in the above series, 3 g of the lauryl ether of polyoxyethylene were added along with the charge. This resulted in an increase of 4–5% in the conversion to hydroxycitronellal. When the operation was shut down after run 16, the cupric oxide catalyst showed the typical black color usually associated with an active system. As hereinbefore set forth, another advantage to the process of the present invention is the small amount and the long life of the catalyst.

EXAMPLE II

In a system similar to that described in Example I, 3,6,7-trimethyl-7-hydroxyoctanol is dehydrogenated to the corresponding aldehyde. The catalyst system also contains calcium carbonate.

EXAMPLE III

In this example, 2-hydroxy-2-cyclohexylethanol is dehydrogenated to 2-hydroxy-2-cyclohexylacetaldehyde. The catalyst system in this run also contains barium carbonate.

I claim as my invention:

1. A process for the continuous liquid phase dehydrogenation of a primary or secondary alcohol which also contains a tertiary hydroxy group said alcohol possessing the following formula:

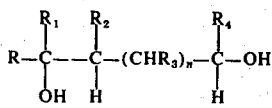

where R and $R_1$ are independently selected from the group consisting of alkyl, aryl, aralkyl and cycloalkyl, $R_2$, $R_3$ and $R_4$ are independently selected from the group consisting of hydrogen, alkyl, aryl, aralkyl and cycloalkyl, and n is an integer of from 0 to 10, to the corresponding aldehyde or ketone without loss of said tertiary hydroxy group, which comprises effecting said dehydrogenation at a temperature of from about 200° to about 350°C. under a vacuum of from about 40 to about 250 mm. Hg. in contact with a stirred suspension of an alcohol dehydrogenation catalyst comprising cupric oxide in a mineral oil having a normal boiling point above about 350°C and an end boiling point within the range of from about 450° to about 550°C, and continuously recovering the aldehyde or ketone.

2. The process of claim 1 wherein said temperature is from about 220° to about 300°C.

3. The process of claim 2 wherein said high boiling liquid is a mineral oil having an initial point above about 300°C.

4. The process of claim 1 wherein said vacuum is from about 90 to about 150 mm Hg.

5. The process of claim 1 wherein said catalyst comprises cupric oxide.

6. The process of claim 1 wherein said alcohol is hydroxycitronellol.

* * * * *